US009316603B2

(12) United States Patent  
Megarity et al.

(10) Patent No.: US 9,316,603 B2
(45) Date of Patent: Apr. 19, 2016

(54) DETECTING THERMAL INTERFACE MATERIAL ('TIM') BETWEEN A HEAT SINK AND AN INTEGRATED CIRCUIT

(75) Inventors: William M. Megarity, Roxboro, NC (US); Luke D. Remis, Raleigh, NC (US); Gregory D. Sellman, Morrisville, NC (US)

(73) Assignee: Lenovo Enterprise Solutions (Singapore) Pte. Ltd., Singapore (SG)

( * ) Notice: Subject to any disclaimer, the term of this patent is extended or adjusted under 35 U.S.C. 154(b) by 980 days.

(21) Appl. No.: 13/469,286

(22) Filed: May 11, 2012

(65) Prior Publication Data

US 2013/0301671 A1    Nov. 14, 2013

(51) Int. Cl.
  *G01N 25/00*    (2006.01)
  *G01N 25/18*    (2006.01)

(52) U.S. Cl.
  CPC ..................... *G01N 25/18* (2013.01)

(58) Field of Classification Search
  USPC .................... 374/7, 44, 45, 29, 141
  See application file for complete search history.

(56) References Cited

U.S. PATENT DOCUMENTS

| 4,867,850 | A | 9/1989 | Oka et al. |
| 6,092,926 | A | 7/2000 | Still et al. |
| 6,923,570 | B2 | 8/2005 | Shih et al. |
| 7,741,834 | B2 | 6/2010 | Dang et al. |
| 7,764,069 | B2 | 7/2010 | Gaynes et al. |
| 7,834,442 | B2 | 11/2010 | Furman et al. |
| 7,961,469 | B2 | 6/2011 | Schmidt et al. |
| 8,026,730 | B2 | 9/2011 | Gaynes et al. |
| 2002/0196835 | A1 | 12/2002 | Schonath et al. |
| 2003/0072349 | A1 | 4/2003 | Osone et al. |
| 2006/0045165 | A1 | 3/2006 | Chan et al. |
| 2008/0040067 | A1 | 2/2008 | Bashor et al. |
| 2008/0075137 | A1 | 3/2008 | Cervantes et al. |
| 2011/0101349 | A1 | 5/2011 | Oda |
| 2011/0267082 | A1 | 11/2011 | Fregeau et al. |
| 2012/0053874 | A1 | 3/2012 | Chainer et al. |
| 2013/0229198 | A1 | 9/2013 | Fregeau et al. |
| 2013/0301670 | A1 | 11/2013 | Megarity et al. |
| 2013/0301671 | A1 | 11/2013 | Megarity et al. |
| 2015/0377809 | A1 | 12/2015 | Megarity et al. |

FOREIGN PATENT DOCUMENTS

JP    2009266862 A    11/2009

OTHER PUBLICATIONS

Office Action, U.S. Appl. No. 13/469,256, filed Mar. 17, 2015, pp. 1-16.

*Primary Examiner* — Mirellys Jagan
(74) *Attorney, Agent, or Firm* — Edward J. Lenart; Katherine S. Brown; Kennedy Lenart Spraggins LLP

(57) ABSTRACT

Detecting TIM between a heat sink and an integrated circuit, the integrated circuit including TIM detection points adapted to receive TIM upon installation of the heat sink and including a TIM detection device configured to be activated upon contact with TIM, including: receiving, upon installation of the heat sink on the integrated circuit and the TIM, TIM in one or more of the TIM detection points; activating, by the TIM in each of the one or more TIM detection points receiving the TIM, a TIM detection device; determining, by a TIM detection module of the integrated circuit in dependence upon the activations of the TIM detection devices, sufficiency of the TIM; and responsive to determining that the TIM between the heat sink and the integrated circuit is insufficient, controlling, in real-time by the TIM detection module, operation of the integrated circuit to reduce heat generated by the integrated circuit.

27 Claims, 15 Drawing Sheets

DETECTING THERMAL INTERFACE MATERIAL ('TIM') BETWEEN A HEAT SINK AND AN INTEGRATED CIRCUIT

BACKGROUND OF THE INVENTION

1. Field of the Invention

The field of the invention is data processing, or, more specifically, methods, apparatus, and products for detecting thermal interface material ('TIM') between a heat sink and an integrated circuit

2. Description of Related Art

As the number of devices on a server or other computer requiring heat sinks increases, determining that each heat sink has sufficient thermal interface material (TIM) becomes more important. Current techniques require the user or manufacturer to tighten the heat sink down and then remove the heat sink to ensure the thermal paste is uniform. Alternatively, an assumption is made that the TIM is sufficient without removal of the heat sink or any further check. The current techniques are manual, time consuming, and an often provide an inaccurate indication of the sufficiency of the TIM. A system that is powered on with insufficient TIM can result in permanent damage to its circuitry.

SUMMARY OF THE INVENTION

Methods, apparatus, products, and heatsinks for detecting TIM between a heat sink and an integrated circuit are disclosed in this specification. The integrated circuit includes a plurality of TIM detection points, each TIM detection point adapted to receive TIM upon installation of the heat sink, each TIM detection point including a TIM detection device configured to be activated upon contact with TIM. Detecting TIM includes: receiving, upon installation of the heat sink on the integrated circuit and the TIM, TIM in one or more of the TIM detection points; activating, by the TIM in each of the one or more TIM detection points receiving the TIM, a TIM detection device; determining, by a TIM detection module of the integrated circuit in dependence upon the activations of the TIM detection devices, sufficiency of the TIM between the heat sink and the integrated circuit; and responsive to determining that the TIM between the heat sink and the integrated circuit is insufficient, controlling, in real-time by the TIM detection module, operation of the integrated circuit to reduce heat generated by the integrated circuit.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION OF EXEMPLARY EMBODIMENTS

Figure 1:
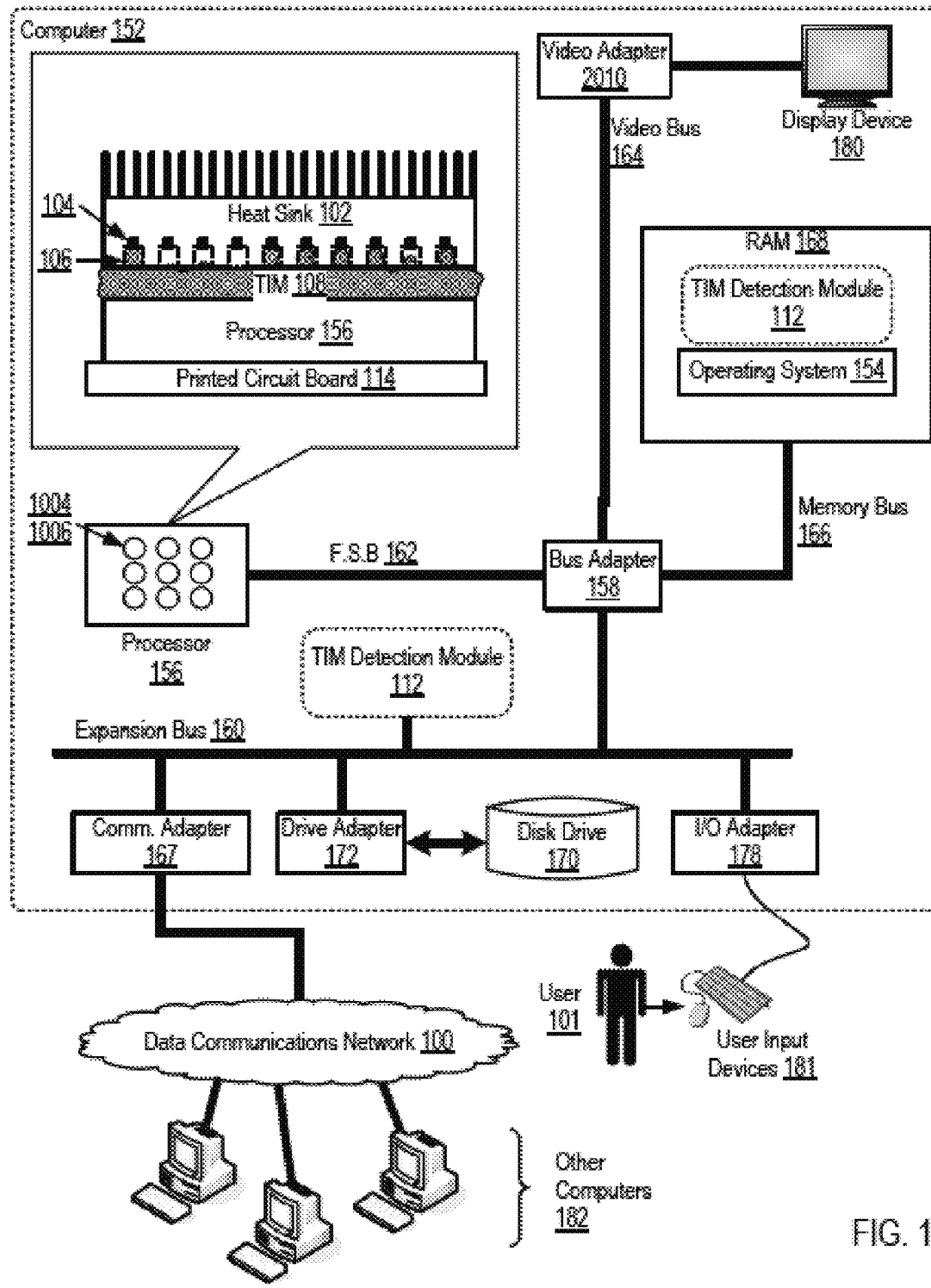
FIG. 1 sets forth a block diagram of a system for TIM between a heat sink and an integrated circuit according to embodiments of the present invention.

Exemplary methods, apparatus, and products for detecting thermal interface material ('TIM') between a heat sink and an integrated circuit in accordance with the present invention are described with reference to the accompanying drawings, beginning with FIG. 1. FIG. 1 sets forth a block diagram of a system for detecting thermal interface material ('TIM') between a heat sink and an integrated circuit according to embodiments of the present invention. The system of FIG. 1 includes automated computing machinery comprising an exemplary computer (152) useful in detecting TIM between a heat sink and an integrated circuit according to embodiments of the present invention. The computer (152) of FIG. 1 includes at least one computer processor (156) or 'CPU' as well as random access memory (168) ('RAM') which is connected through a high speed memory bus (166) and bus adapter (158) to processor (156) and to other components of the computer (152).

The processor (156) is an example of an integrated circuit upon which TIM (108) and a heat sink (102) may be installed. The example of FIG. 1 sets forth two implementations configured to detect TIM between a heat sink and the processor (156). In one implementation the heat sink (102) is configured to detect TIM (108) between a heat sink and the processor (156). In another implementation, the processor (156) itself detects the TIM (108).

In the first implementation, the heat sink (102) includes a plurality of TIM detection points (106). A TIM detection point as the term is used here is a receptacle adapted to receive TIM upon installation of the heat sink. When the heat sink (102) is installed on the TIM, the TIM seeps into the TIM detection points (106). Each TIM detection point (106) includes a TIM detection device configured to be activated upon contact with TIM. That is, upon installation of the heat sink (102) on the processor (156) and the TIM (108), one or more of the TIM detection points receives the TIM.

The TIM (108) activates a TIM detection device (104) in each of the one or more TIM detection points receiving the TIM (108). A TIM detection module (112) determines, in dependence upon the activations of the TIM detection devices (104), sufficiency of the TIM between the heat sink and the integrated circuit. The TIM detection module (112) in the example of FIG. 1 is depicted as a discrete component of the computer (152) coupled to the expansion bus (160) for clarity of explanation, not limitation. Readers of skill in the art will recognize that such a device may be implemented in a variety of ways including, for example, as a service processor, as an FPGA, and as other devices, coupled to the TIM detection devices (104) through an out-of-band bus. If the TIM is insufficient, the TIM detection module (112) may notify a user (101).

In a second implementation, the processor (156) itself includes a plurality of TIM detection points (1006). In this implementation, like the last, each TIM detection point (1006) is adapted to receive TIM upon installation of the heat sink (102). Each TIM detection point (1006) also includes a TIM detection device (1004) that is configured to be activated upon contact with TIM. In this second example implementation, upon installation of the heat sink on the processor (156) and the TIM (108), TIM (108) is received in one or more of the TIM detection points (106). The TIM (108) activates, a TIM detection device (1004) in each of the one or more TIM detection points (1006) receiving the TIM (108).

A TIM detection module implemented as a module of computer program instructions stored in RAM (168) determines in dependence upon the activations of the TIM detection devices (1006), sufficiency of the TIM between the heat sink and the processor (156). Responsive to determining that the TIM (108) between the heat sink (102) and the processor (156) is insufficient, the TIM detection module (112) controls, in real-time, operation of the processor (156) to reduce heat generated by the processor (156). Although the TIM detection module (112) is depicted in this example implementation as a module of computer program instructions stored in RAM (168), readers of skill in the art will recognize that such a module may also be implemented as hardware within the processor (156) itself, as a combination of hardware and software separate from the processor (156) and RAM (168), and in other ways.

In addition to the TIM detection module (112), an operating system (154) is also stored in RAM (168). Operating systems useful in systems that detect TIM between a heat sink and an integrated circuit according to embodiments of the present invention include UNIX™, Linux™, Microsoft XP™, AIX™, IBM's i5/OS™, and others as will occur to those of skill in the art. The operating system (154) and TIM detection module (112) in the example of FIG. 1 are shown in RAM (168), but many components of such software typically are stored in non-volatile memory also, such as, for example, on a disk drive (170).

The computer (152) of FIG. 1 includes disk drive adapter (172) coupled through expansion bus (160) and bus adapter (158) to processor (156) and other components of the computer (152). Disk drive adapter (172) connects non-volatile data storage to the computer (152) in the form of disk drive (170). Disk drive adapters useful in computers that detect TIM between a heat sink and an integrated circuit according to embodiments of the present invention include Integrated Drive Electronics ('IDE') adapters, Small Computer System Interface ('SCSI') adapters, and others as will occur to those of skill in the art. Non-volatile computer memory also may be implemented for as an optical disk drive, electrically erasable programmable read-only memory (so-called 'EEPROM' or 'Flash' memory), RAM drives, and so on, as will occur to those of skill in the art.

The example computer (152) of FIG. 1 includes one or more input/output ('I/O') adapters (178). I/O adapters implement user-oriented input/output through, for example, software drivers and computer hardware for controlling output to display devices such as computer display screens, as well as user input from user (101) input devices (181) such as keyboards and mice. The example computer (152) of FIG. 1 includes a video adapter (209), which is an example of an I/O adapter specially designed for graphic output to a display device (180) such as a display screen or computer monitor. Video adapter (209) is connected to processor (156) through a high speed video bus (164), bus adapter (158), and the front side bus (162), which is also a high speed bus.

The exemplary computer (152) of FIG. 1 includes a communications adapter (167) for data communications with other computers (182) and for data communications with a data communications network (100). Such data communications may be carried out serially through RS-232 connections, through external buses such as a Universal Serial Bus ('USB'), through data communications networks such as IP data communications networks, and in other ways as will occur to those of skill in the art. Communications adapters implement the hardware level of data communications through which one computer sends data communications to another computer, directly or through a data communications network. Examples of communications adapters useful in systems that detect TIM between a heat sink and an integrated circuit according to embodiments of the present invention include modems for wired dial-up communications, Ethernet (IEEE 802.3) adapters for wired data communications, and 802.11 adapters for wireless data communications.

The arrangement of computers and other devices making up the exemplary system illustrated in FIG. 1 are for explanation, not for limitation. Data processing systems useful according to various embodiments of the present invention may include additional servers, routers, other devices, and peer-to-peer architectures, not shown in FIG. 1, as will occur to those of skill in the art. Networks in such data processing systems may support many data communications protocols, including for example TCP (Transmission Control Protocol), IP (Internet Protocol), HTTP (HyperText Transfer Protocol), WAP (Wireless Access Protocol), HDTP (Handheld Device Transport Protocol), and others as will occur to those of skill in the art. Various embodiments of the present invention may be implemented on a variety of hardware platforms in addition to those illustrated in FIG. 1.

Figure 2:
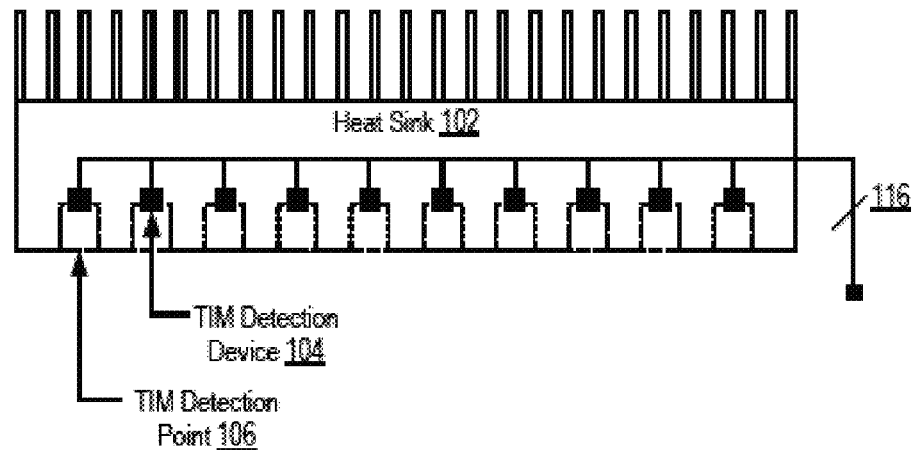
FIG. 2 sets forth a perspective view of an example system configured for TIM detection in accordance with embodiments of the present invention, prior to installation of a heat sink on an integrated circuit and TIM.
Figure 2:
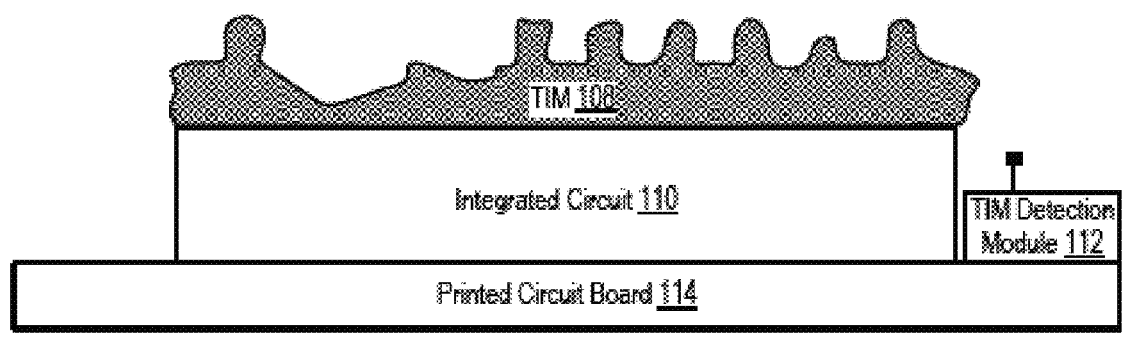

For further explanation, FIG. 2 sets forth a perspective view of an example system configured for TIM detection in accordance with embodiments of the present invention, prior to installation of a heat sink (102) on an integrated circuit (110) and TIM (108). The example system of FIG. 2 includes a heat sink (102), an integrated circuit (110) installed on a printed circuit board ('PCB') (114), and TIM (108) applied to the integrated circuit (110). The example heat sink (102) of FIG. 2 is adapted for TIM detection in accordance with embodiments of the present invention and includes a plurality of TIM detection points (106). Each TIM detection point (106) is adapted to receive TIM upon installation of the heat sink (102) on the integrated circuit (110) and the TIM (108). Each TIM detection point (106) in the example heat sink (102) of FIG. 2 includes a TIM detection device (104) activated upon contact with TIM (108) and providing a TIM detection signal (116) to a TIM detection module (112) upon activation for determination of the sufficiency of the TIM (108) between the heat sink and the integrated circuit.

Figure 3:
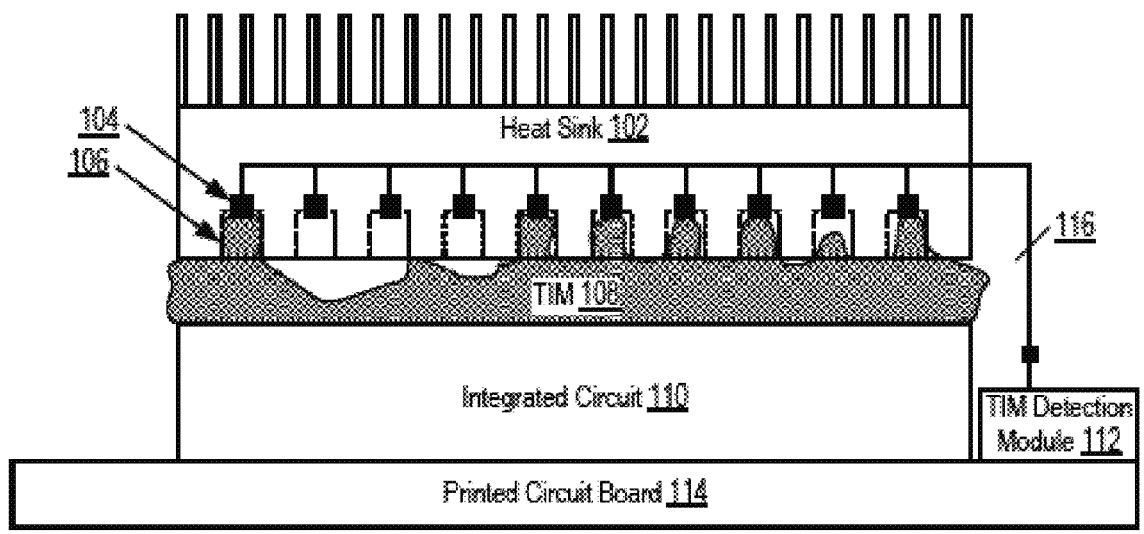
FIG. 3 sets forth a perspective view of the example system of FIG. 2, after installation of a heat sink on an integrated circuit and TIM.

For further explanation, FIG. 3 sets forth a perspective view of the example system of FIG. 2, after installation of a heat sink (102) on an integrated circuit (110) and TIM (108). The example system of FIG. 3 depicts the same system of FIG. 2, after installation of the heat sink. The TIM detection signals (116) of the heat sink couple to the TIM detection module (112) upon installation. Also upon installation of the heat sink (102) in the example of FIG. 3, TIM (108) is received in a number of the TIM detection points (106).

In each of the one or more TIM detection points (106) receiving the TIM, the TIM (108) activates a TIM detection device (104). Upon such activation, the TIM detection device (104) sends a TIM detection signal (116) to the TIM detection module (112). The TIM detection module (112) determines sufficiency of the TIM (108) between the heat sink (102) and the integrated circuit (110).

Figure 4:
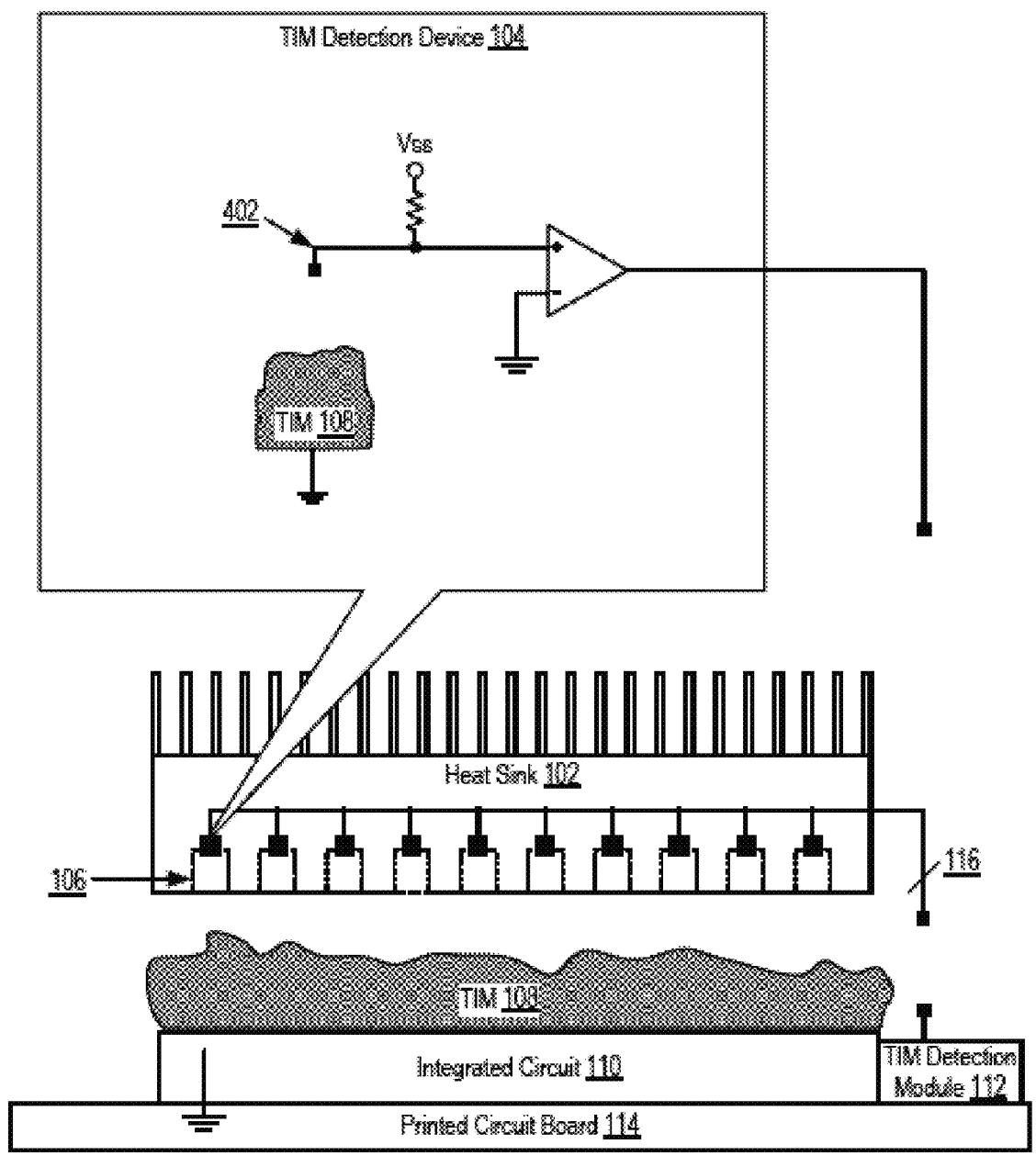
FIG. 4 sets forth a perspective view of another example system configured for TIM detection in accordance with embodiments of the present invention, prior to installation of a heat sink.

TIM detection devices (104) may be implemented in a variety of ways. For further explanation, therefore, FIG. 4 sets forth a perspective view of another example system configured for TIM detection in accordance with embodiments of the present invention, prior to installation of a heat sink. The system of FIG. 4 is similar to the system of FIG. 2 in that the system of FIG. 4 includes a heat sink (102), an integrated circuit (110) installed on a PCB (114), and TIM (108) applied to the integrated circuit (110). The heat sink (102) includes a plurality of TIM detection points (106), with each TIM detection point (106) including a TIM detection device (104) activated upon contact with TIM (108) and providing a TIM detection signal (116) to a TIM detection module (112) upon activation for determination of the sufficiency of the TIM (108) between the heat sink and the integrated circuit.

The example system of FIG. 4, however, differs from the system of FIG. 2 in that in the example system of FIG. 4, a casing of the integrated circuit is electrically coupled to a ground voltage and the TIM is electrically conductive and is electrically coupled to the integrated circuit casing. That is, the TIM is grounded through the integrated circuit (110) and the PCB (114).

In the example system of FIG. 4, each TIM detection device (104) includes an electrical probe (402). The electrical probe (402) has a source voltage (Vss) prior to electrically coupling to the TIM (108). The TIM detection device (104) is activated upon contact with the TIM (108) by electrically coupling the electrical probe (402) to the TIM (108), the integrated circuit (110) casing, and the ground voltage.

Figure 5:
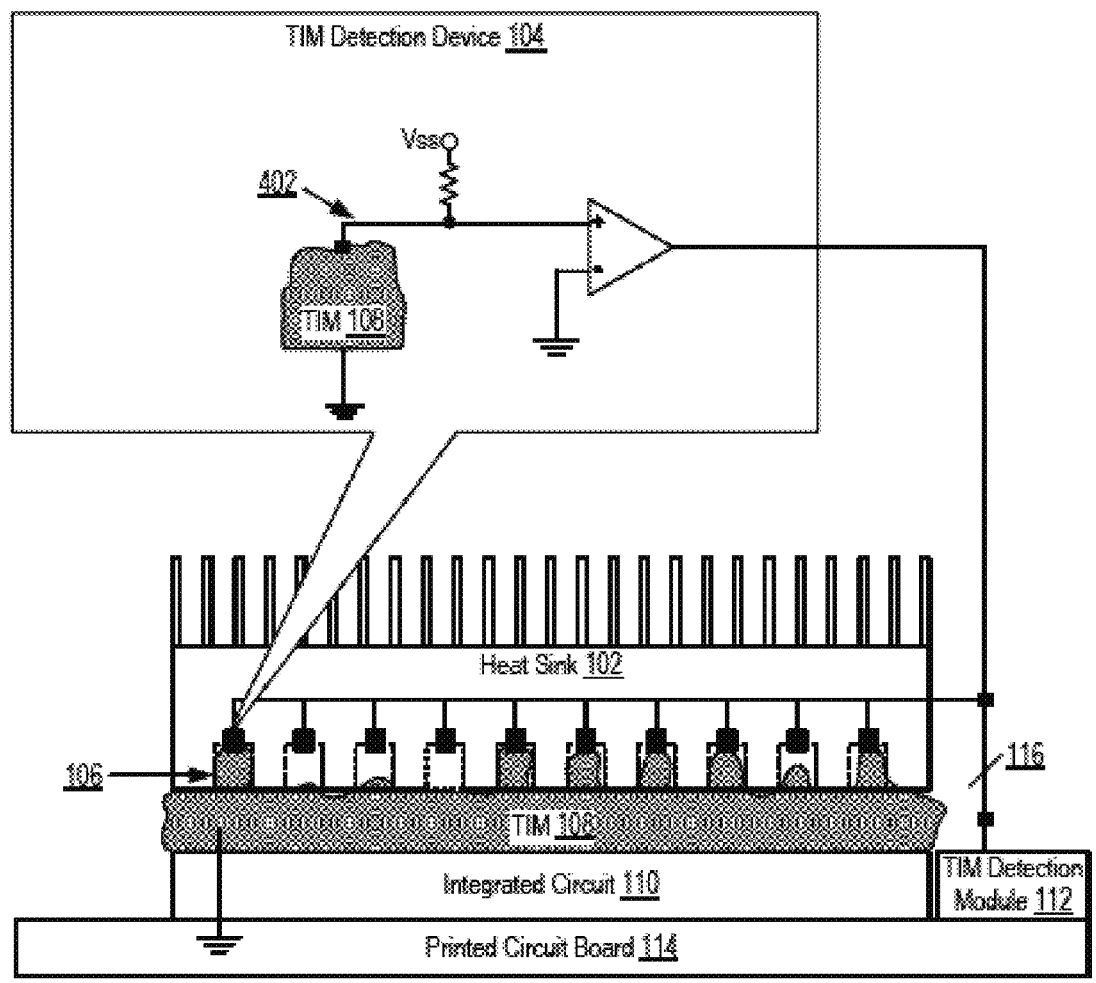
FIG. 5 sets forth a perspective view of the example system of FIG. 4, after installation of the heat sink.

For further explanation, FIG. 5 sets forth a perspective view of the example system of FIG. 4, after installation of the heat sink. In the example of FIG. 5, upon installation of the heat sink (102) on the integrated circuit (110) and the TIM (108), TIM (108) is received in one or more of the TIM detection points (106) and the TIM (108) activates a TIM detection device (104) in each of the TIM detection points receiving the TIM (108). In the example of FIG. 5, activating a TIM detection device (104) includes electrically coupling, by the TIM (108), the electrical probe (402) to the integrated circuit (110) casing and the ground voltage. By electrically coupling the electrical probe (402) to the ground voltage, the voltage level at the electrical probe (402) is altered from the source voltage (Vss) to the ground voltage.

The TIM detection module (112) determines sufficiency of the TIM between the heat sink and the integrated circuit by detecting, for each TIM detection point (104) receiving the TIM (108), the alteration of the voltage level of each electrical probe. In this example a comparator compares the voltage at the electrical probe to a ground voltage. When the electrical probe is at the source voltage (Vss) the comparator outputs a logic high signal (116). When the electrical probe is coupled to the ground voltage by the TIM (108), the comparator outputs a logic low signal (116).

Figure 6:
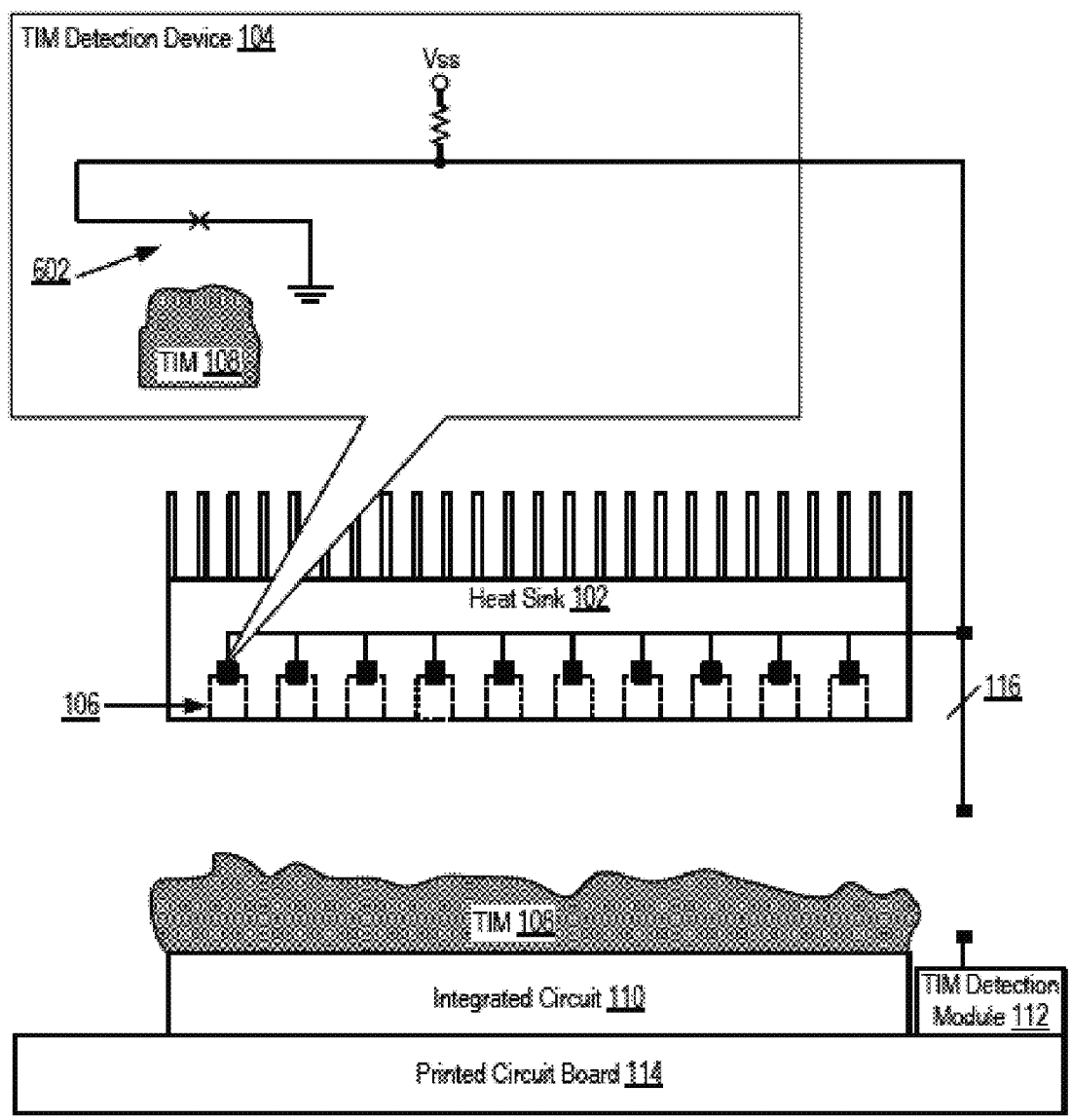
FIG. 6 sets forth a perspective view of another example system configured for TIM detection in accordance with embodiments of the present invention, prior to installation of a heat sink.

As mentioned above, TIM detection devices (104) may be implemented in other ways. For further explanation, therefore, FIG. 6 sets forth a perspective view of another example system configured for TIM detection in accordance with embodiments of the present invention, prior to installation of a heat sink. The system of FIG. 6 is similar to the system of FIG. 2 in that the system of FIG. 6 includes a heat sink (102), an integrated circuit (110) installed on a PCB (114), and TIM (108) applied to the integrated circuit (110). The heat sink (102) includes a plurality of TIM detection points (106), with each TIM detection point (106) including a TIM detection device (104) activated upon contact with TIM (108) and providing a TIM detection signal (116) to a TIM detection module (112) upon activation for determination of the sufficiency of the TIM (108) between the heat sink and the integrated circuit.

The system of FIG. 6 differs from the system of FIG. 2, however, in that in the system of FIG. 6, each TIM detection device (104) includes a mechanical switch (602). The mechanical switch is closed prior to contact with the TIM (108). In the example of FIG. 6, the mechanical switch (602) is coupled to ground voltage when closed. The TIM detection device is activated by physically opening, by the TIM (108), the mechanical switch.

Figure 7:
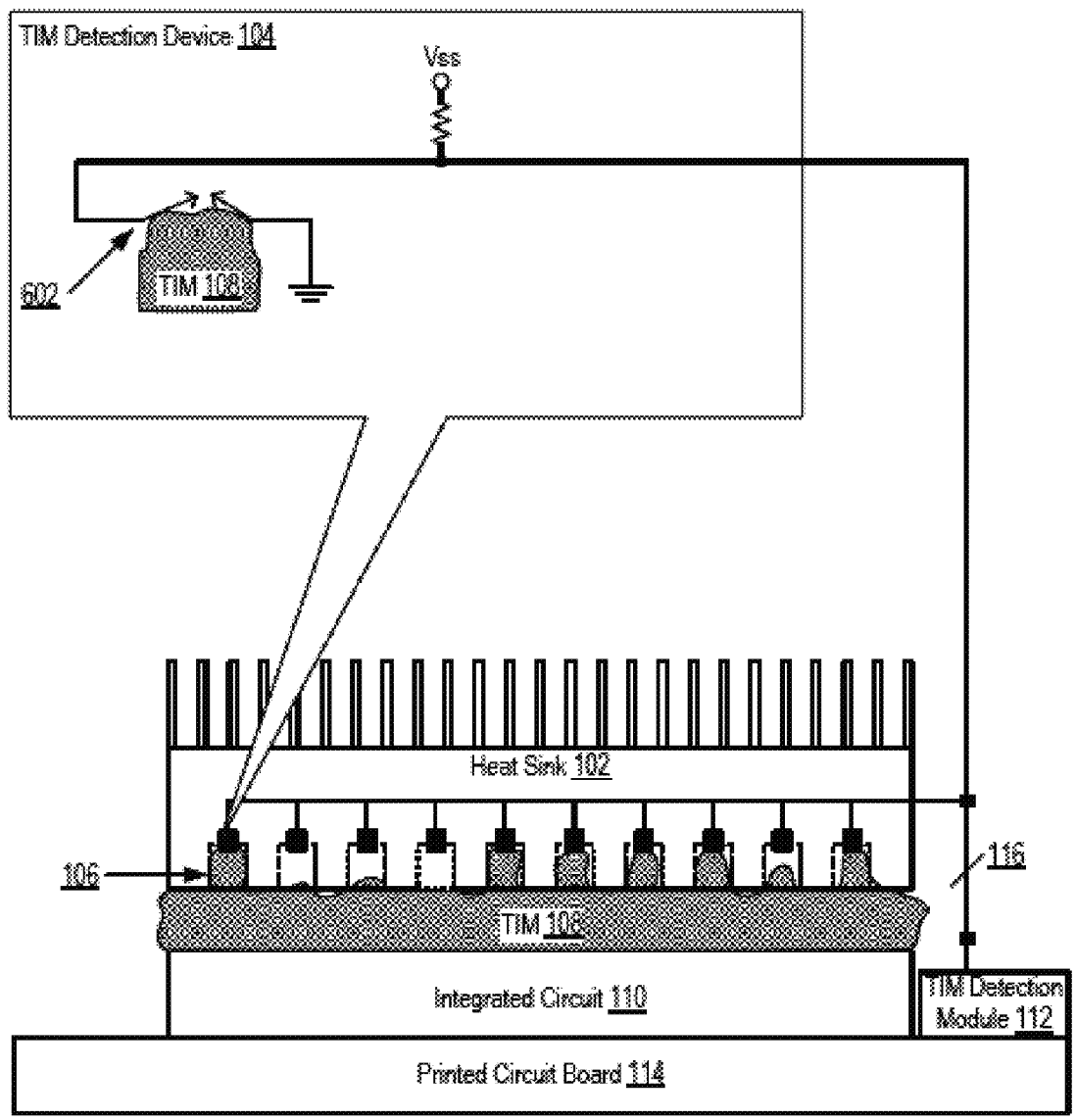
FIG. 7 sets forth a perspective view of the example system of FIG. 6, after installation of the heat sink.

For further explanation, FIG. 7 sets forth a perspective view of the example system of FIG. 6, after installation of the heat sink. In the example of FIG. 7, upon installation of the heat sink (102) on the integrated circuit (110) and the TIM (108), TIM (108) is received in one or more of the TIM detection points (106) and the TIM (108) activates a TIM detection device (104) in each of the TIM detection points receiving the TIM (108). In the example of FIG. 7, activating a TIM detection device (104) includes physically opening the mechanical switch (602) by the TIM (108). As mentioned above, the mechanical switch (602) is coupled to ground voltage when closed. The voltage experienced on the signal line (116) by the TIM detection module (112), therefore, prior to contact between the TIM and the mechanical switch, is a ground voltage. After the TIM physically opens the mechanical switch (602, the voltage experienced on the signal line (116) by the TIM detection module (112) is a source voltage (Vss). The alternation between a ground voltage and the source voltage indicates to the TIM detection module (112)

that TIM is present in the TIM detection point that includes the opened mechanical switch.

Figure 8:
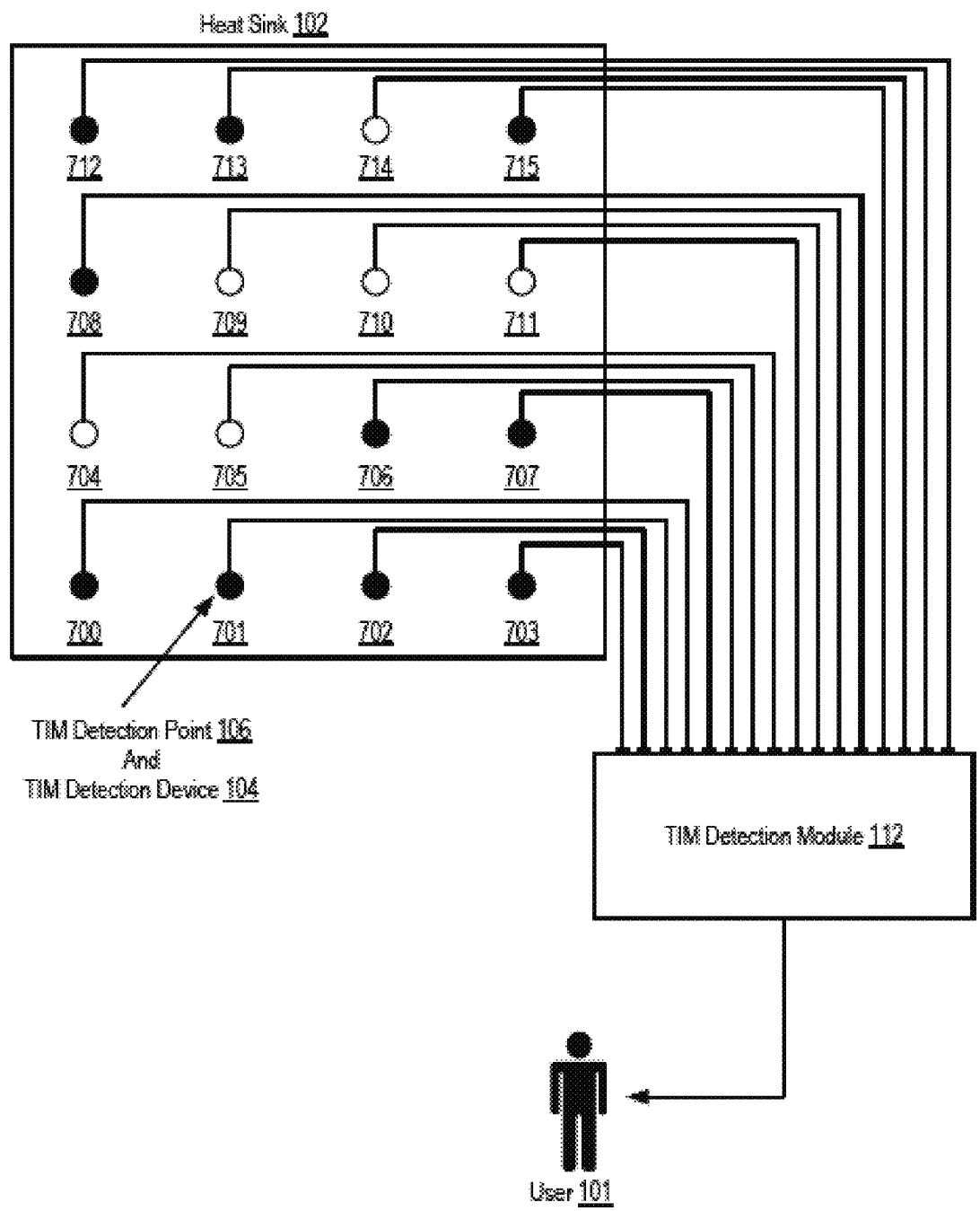
FIG. 8 sets forth a block diagram of an example system for detecting TIM between a heat sink and integrated circuit in accordance with embodiments of the present invention, where the heat sink includes TIM detection points configured to indicate a coverage area of TIM.

The TIM detection modules of the previous figures may be configured to determine sufficiency of the TIM between the heat sink and the integrated circuit in various ways. In one embodiment, a TIM detection module may determine whether the number of activated TIM detection devices exceeds a predetermined threshold. In this embodiment, the TIM detection module determines whether some minimum amount of TIM has been applied to the integrated circuit, regardless of the location of the TIM on the integrated circuit. In another embodiment, the TIM detection device may, determine whether the positions of the activated TIM detection devices indicate a sufficient coverage area of the TIM. For further explanation, therefore, FIG. 8 sets forth a block diagram of an example system for detecting TIM between a heat sink and integrated circuit in accordance with embodiments of the present invention, where the heat sink includes TIM detection points configured to indicate a coverage area of TIM. The example system of FIG. 8 depicts a view of the bottom of a heat sink (102) configured with a plurality of TIM detection points (106), with each TIM detection point adapted to receive TIM upon installation of the heat sink (102) and each TIM detection point (106) including a TIM detection device (104) configured to be activated upon contact with TIM. In the example of FIG. 8, the heat sink (102) includes sixteen TIM detection points (700-715), arranged in a grid. The TIM detection points that are shaded (700-703, 706-707, 708, 712-713, and 715) indicate an activated TIM detection device (104)—and thus, sufficient TIM at that physical location on the integrated circuit—and those TIM detection points that are not shaded (704-705, 709-711, and 714) indicate insufficient TIM at that physical location on the integrated circuit.

More than half of the TIM detection devices are activated in the heat sink. In an implementation in which only a predefined number of TIM detection devices need be activated to indicate sufficient TIM on the integrated circuit, the TIM detection module (112) may determine that the TIM is sufficient. Given the physical layout of the non-activated TIM detection devices (704-705, 709-711, and 714)—namely the center of the integrated circuit—the TIM may, in fact, be insufficient. In this example, the TIM detection module (112) utilizes not only the number of active TIM detection devices, but also the physical location of the active (and non-active) TIM detection devices (104) to determine whether the positions of the activated TIM detection devices indicate a sufficient coverage area of the TIM. If the TIM detection module (112) determines that the TIM is insufficient, the module (112) may notify the user (101) of the insufficiency.

Figure 9:
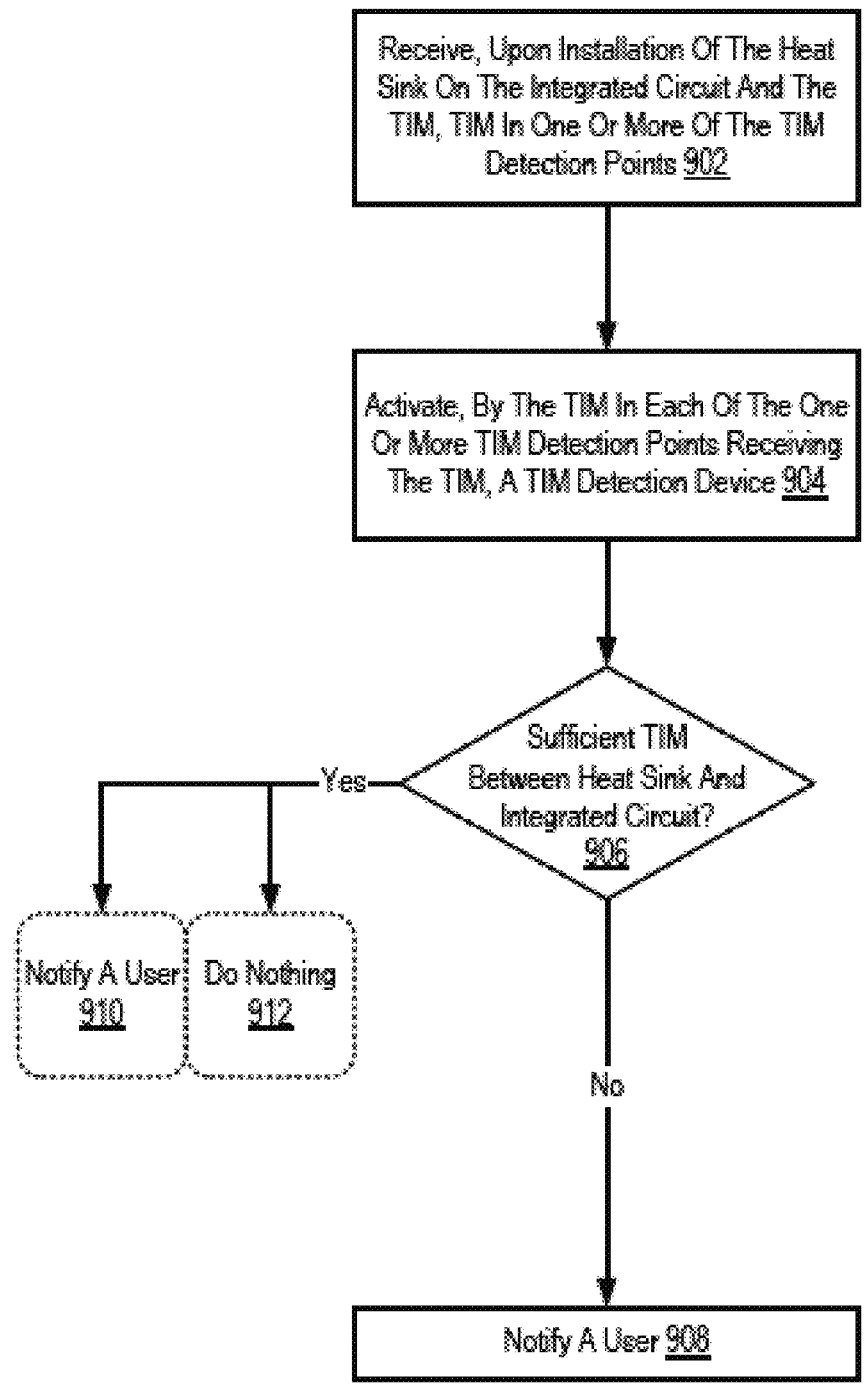
FIG. 9 sets forth a flow chart illustrating an exemplary method for detecting TIM between a heat sink and an integrated circuit according to embodiments of the present invention.

For further explanation, FIG. 9 sets forth a flow chart illustrating an exemplary method for detecting TIM between a heat sink and an integrated circuit according to embodiments of the present invention. The example method of FIG. 9 is carried out in a system similar to that depicted in the examples of FIGS. 2 and 3 which includes a heat sink and an integrated circuit, where the heat sink includes a plurality of TIM detection points, each TIM detection point is adapted to receive TIM upon installation of the heat sink, and each TIM detection point includes a TIM detection device configured to be activated upon contact with TIM.

The method of FIG. 9 includes receiving (902), upon installation of the heat sink on the integrated circuit and the TIM, TIM in one or more of the TIM detection points; activating (904), by the TIM in each of the one or more TIM detection points receiving the TIM, a TIM detection device; and determining (906), by a TIM detection module in dependence upon the activations of the TIM detection devices, sufficiency of the TIM between the heat sink and the integrated circuit.

If the TIM detection module determines that the TIM is sufficient, the method of FIG. 9 continues by either notifying (910) a user of the sufficiency of the TIM or doing nothing. Responsive to determining insufficiency of the TIM, the method of FIG. 9 continues by notifying (908), by the TIM detection module, a user of the insufficiency. The TIM detection module may notify a user in a number of ways, by storing an indication in a log file, by sending a data communications message to a predefined target address, by activating a visual indication such as a Light Emitting Diode ('LED'), and so on as will occur to readers of skill in the art.

In the method of FIG. 9, determining (906) sufficiency of the TIM between the heat sink and the integrated circuit may be carried out by determining whether the number of activated TIM detection devices exceeds a predetermined threshold, determining whether the positions of the activated TIM detection devices indicate a sufficient coverage area of the TIM, or both.

In some embodiments, a casing of the integrated circuit is electrically coupled to a ground voltage, the TIM is electrically conductive and is electrically coupled to the integrated circuit casing, and each TIM detection device includes an electrical probe, the electrical probe having a source voltage prior to electrically coupling to the TIM. In such an embodiment, activating (904) the TIM detection device may be carried out by electrically coupling, by the TIM, the electrical probe to the integrated circuit casing and the ground voltage, altering the voltage level at the electrical probe from the source voltage to the ground voltage. Determining (906) sufficiency of the TIM between the heat sink and the integrated circuit in such an embodiment may be carried out by detecting, for each TIM detection point receiving the TIM, the alteration of the voltage level of each electrical probe.

In some embodiments, each TIM detection device includes a mechanical switch that is closed prior to receiving TIM. In such an embodiment, activating (904) the TIM detection device may be carried out by physically opening, by the TIM, the mechanical switch. Determining (906) sufficiency of the TIM between the heat sink and the integrated circuit in such an embodiment may be carried out by detecting the opening of each mechanical switch activated upon receiving the TIM in the TIM detection point.

FIGS. 2-9 describe an implementation in which TIM detection points and TIM detection devices are implemented in a heat sink. As explained above with respect to FIG. 1, such TIM detection points and TIM detection devices may also be implemented as part of an integrated circuit, such as processor. For further explanation, therefore, FIG. 10A sets forth a perspective view of an example system configured for TIM detection in accordance with embodiments of the present invention, prior to installation of a heat sink on an integrated circuit and TIM, where the integrated circuit includes TIM detection points and TIM detection devices.

Figure 10A:
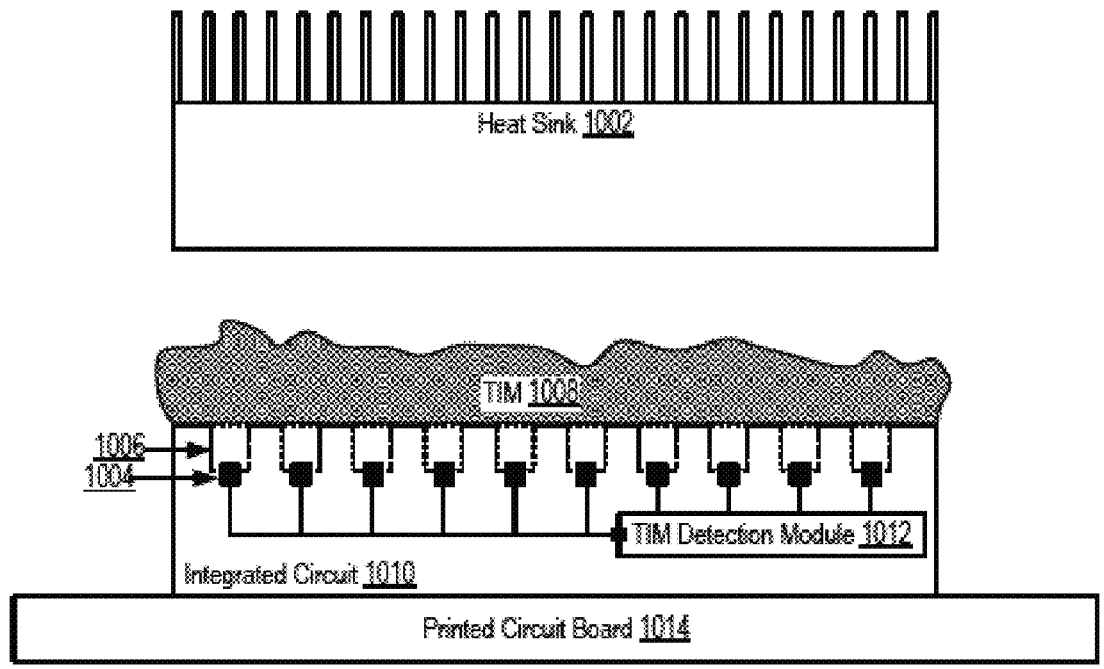
FIG. 10A sets forth a perspective view of an example system configured for TIM detection in accordance with embodiments of the present invention, prior to installation of a heat sink on an integrated circuit and TIM, where the integrated circuit includes TIM detection points and TIM detection devices.

The example system of FIG. 10A includes a heat sink (1002), an integrated circuit (1010) installed on a printed circuit board ('PCB') (1014), and TIM (1008) applied to the integrated circuit (1010). The example integrated circuit (1010) of FIG. 10A is adapted for TIM detection in accordance with embodiments of the present invention and includes a plurality of TIM detection points (1006). Each TIM detection point (1006) is adapted to receive TIM upon installation of the heat sink (1002) on the integrated circuit (1010) and the TIM (1008). Each TIM detection point (1006) in the example integrated circuit (1002) of FIG. 10A includes a TIM detection device (1004) activated upon contact with TIM (1008) and providing a TIM detection signal to a TIM detection module (1012) upon activation for determination of the sufficiency of the TIM (1008) between the heat sink and the integrated circuit.

Figure 10B:
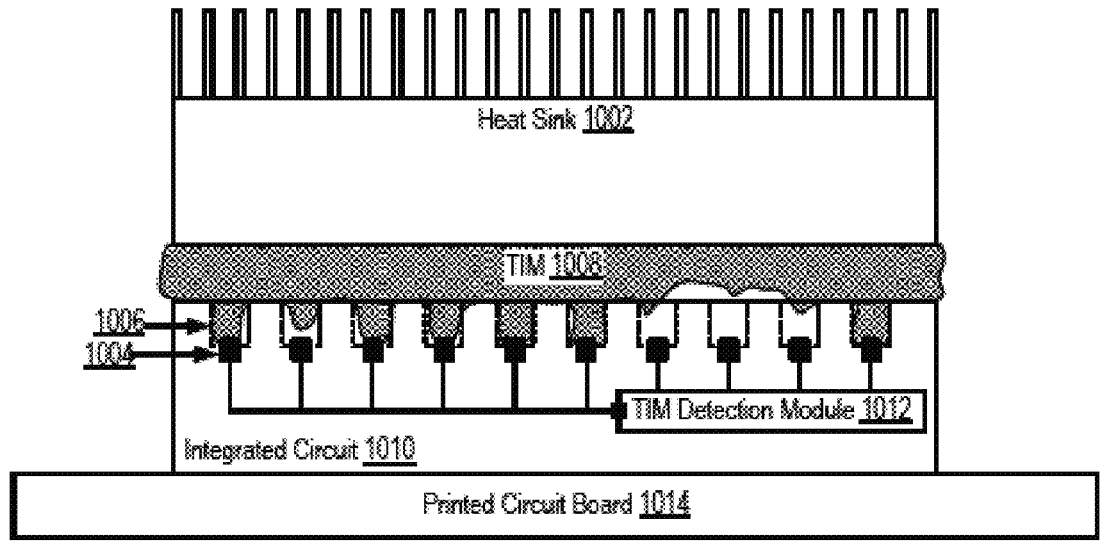
FIG. 10B sets forth a perspective view of the example system of FIG. 10A, after installation of a heat sink on an integrated circuit and TIM.

For further explanation, FIG. 10B sets forth a perspective view of the example system of FIG. 10A, after installation of a heat sink (1002) on an integrated circuit (1010) and TIM (1008). The example system of FIG. 10B depicts the same system of FIG. 10A, after installation of the heat sink. Upon installation of the heat sink (1002) in the example of FIG. 10B, TIM (1008) is received in a number of the TIM detection points (1006).

In each of the one or more TIM detection points (1006) receiving the TIM, the TIM (1008) activates a TIM detection device (1004). Upon such activation, the TIM detection device (1004) sends a TIM detection signal to the TIM detection module (1012) of the integrated circuit. The TIM detection module (1012) determines sufficiency of the TIM (1008) between the heat sink (1002) and the integrated circuit (1010). Responsive to determining that the TIM between the heat sink and the integrated circuit is insufficient, the TIM detection module (1012) controls, in real-time, operation of the integrated circuit (1010) to reduce heat generated by the integrated circuit.

Figure 11:
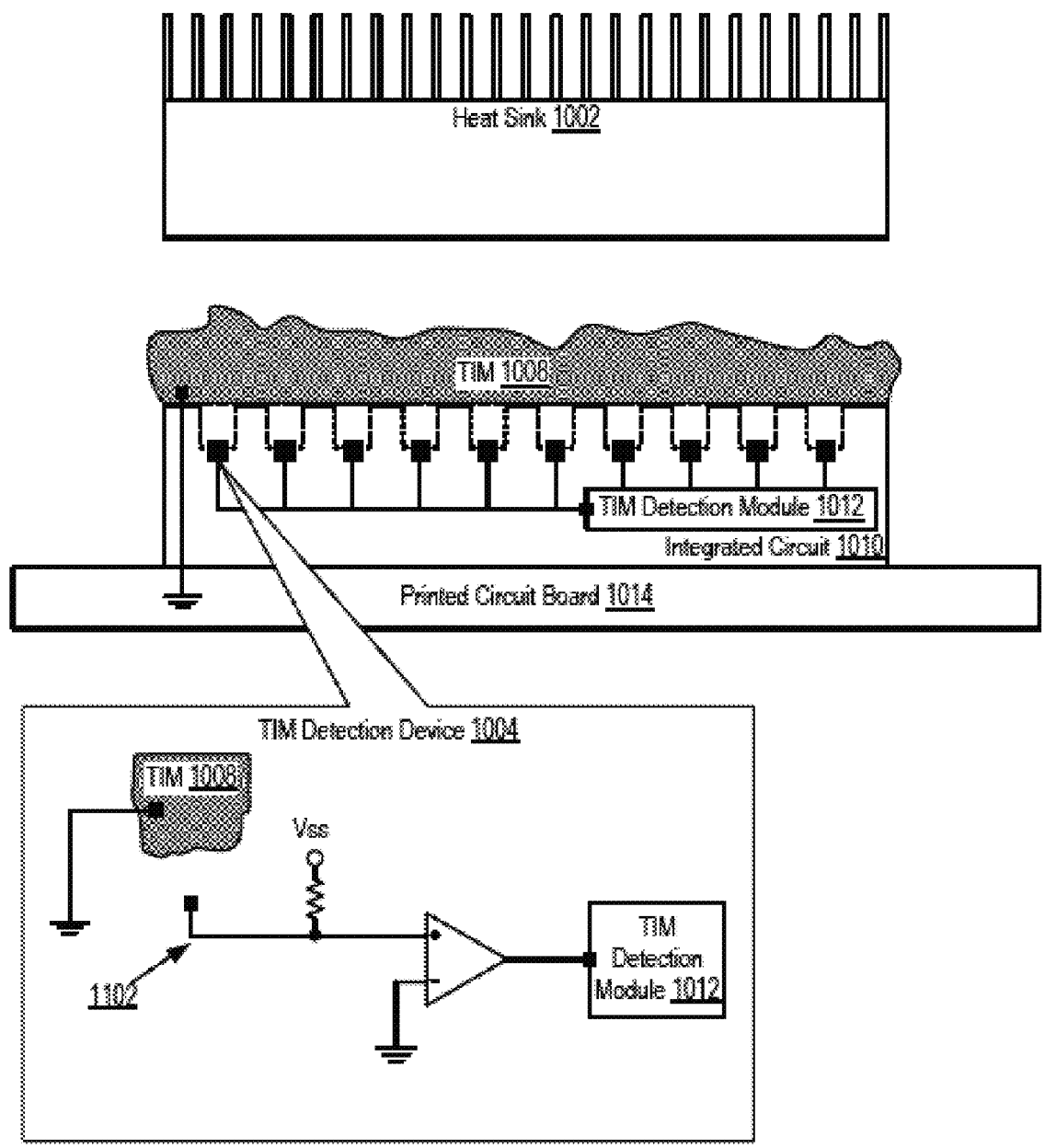
FIG. 11 sets forth a perspective view of another example system configured for TIM detection in accordance with embodiments of the present invention, prior to installation of a heat sink.

TIM detection devices (1004) may be implemented in an integrated circuit (1010) in a variety of ways. For further explanation, therefore, FIG. 11 sets forth a perspective view of another example system configured for TIM detection in accordance with embodiments of the present invention, prior to installation of a heat sink. The system of FIG. 11 is similar to the system of FIG. 10A in that the system of FIG. 11 includes a heat sink (1002), an integrated circuit (1010) installed on a PCB (1014), and TIM (1008) applied to the integrated circuit (1010). The integrated circuit (1002) includes a plurality of TIM detection points (1006), with each TIM detection point (1006) including a TIM detection device (1004) activated upon contact with TIM (1008) and providing a TIM detection signal to a TIM detection module (1012) of the integrated circuit upon activation for determination of the sufficiency of the TIM (1008) between the heat sink and the integrated circuit.

The example system of FIG. 11, however, differs from the system of FIG. 10A in that in the example system of FIG. 11, a casing of the integrated circuit (1010) is electrically coupled to a ground voltage and the TIM (1008) is electrically conductive and is electrically coupled to the integrated circuit casing. That is, the TIM is grounded through the integrated circuit (1010) and the PCB (1014).

In the example system of FIG. 11, each TIM detection device (1004) includes an electrical probe (1102). The electrical probe (1102) has a source voltage (Vss) prior to electrically coupling to the TIM (1008). The TIM detection device (1104) is activated upon contact with the TIM (1008) by electrically coupling the electrical probe (1102) to the TIM (1008), the integrated circuit (1010) casing, and the ground voltage.

Figure 12:
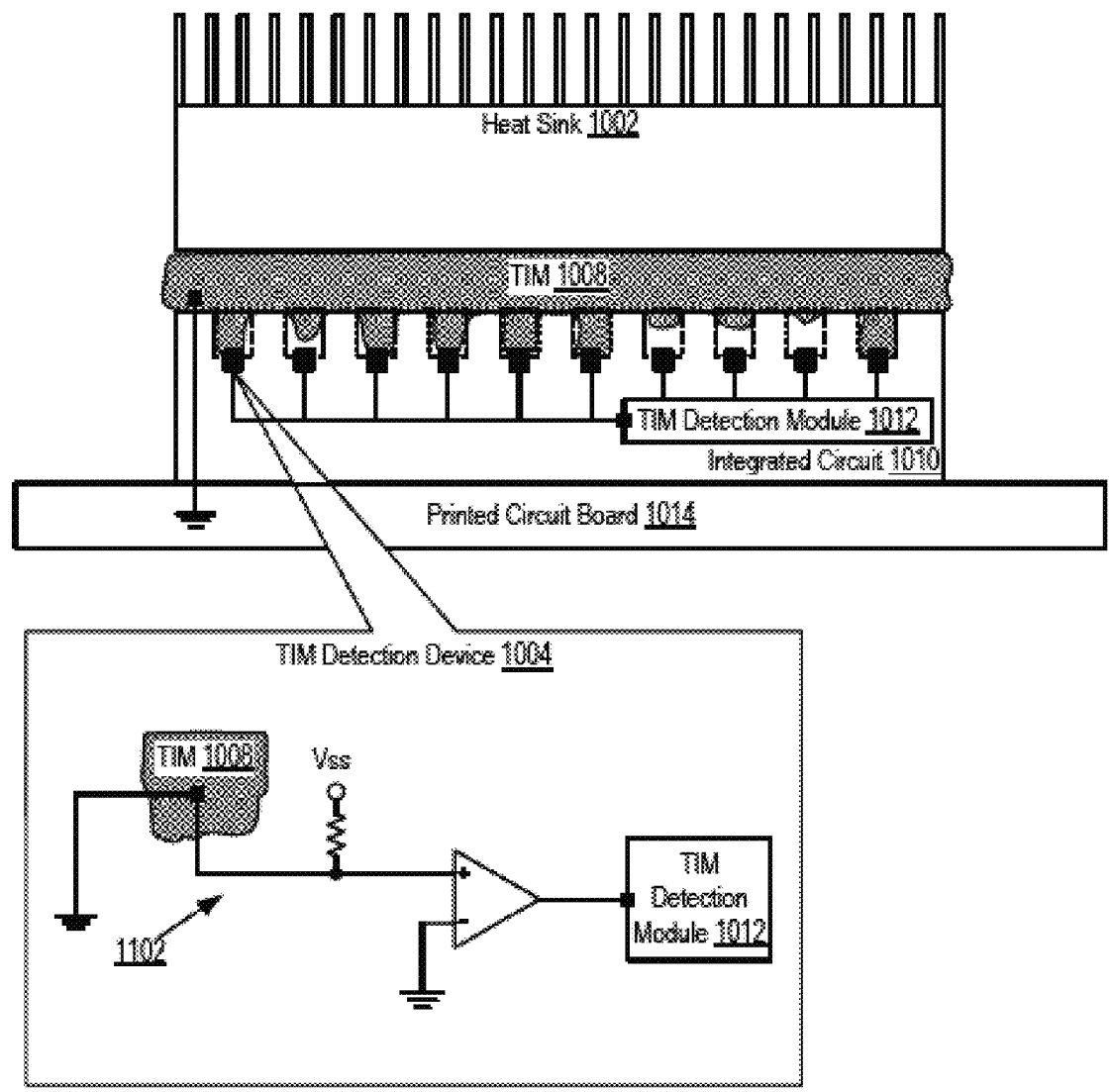
FIG. 12 sets forth a perspective view of the example system of FIG. 11, after installation of the heat sink.

For further explanation, FIG. 12 sets forth a perspective view of the example system of FIG. 11, after installation of the heat sink. In the example of FIG. 12, upon installation of the heat sink (1002) on the integrated circuit (1010) and the TIM (1008), TIM (1008) is received in one or more of the TIM detection points (1006) and the TIM (1008) activates a TIM detection device (1004) in each of the TIM detection points receiving the TIM (1008). In the example of FIG. 12, activating a TIM detection device (1004) includes electrically coupling, by the TIM (1008), the electrical probe (1102) to the integrated circuit (1010) casing and the ground voltage. By electrically coupling the electrical probe (1102) to the ground voltage, the voltage level at the electrical probe (1102) is altered from the source voltage (Vss) to the ground voltage.

The TIM detection module (1012) determines sufficiency of the TIM between the heat sink and the integrated circuit by detecting, for each TIM detection point (1004) receiving the TIM (1008), the alteration of the voltage level of each electrical probe. In this example a comparator compares the voltage at the electrical probe to a ground voltage. When the electrical probe is at the source voltage (Vss) the comparator outputs a logic high signal to the TIM detection module (1012). When the electrical probe is coupled to the ground voltage by the TIM (1008), the comparator outputs a logic low signal (1016).

Figure 13:
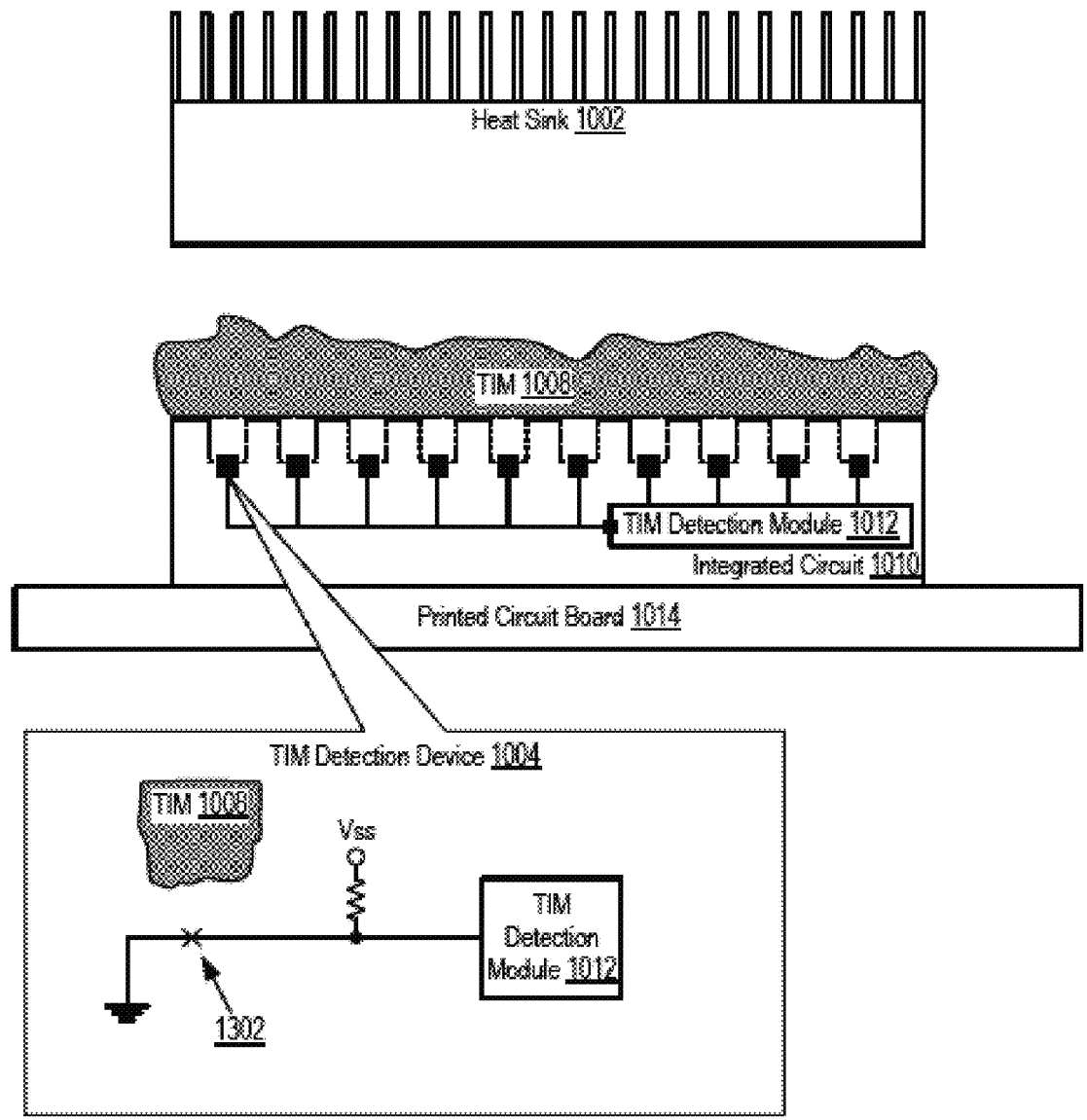
FIG. 13 sets forth a perspective view of another example system configured for TIM detection in accordance with embodiments of the present invention, prior to installation of a heat sink.

TIM detection devices (1004) may be implemented in integrated circuits (1010) in other ways as well. For further explanation, therefore, FIG. 13 sets forth a perspective view of another example system configured for TIM detection in accordance with embodiments of the present invention, prior to installation of a heat sink. The system of FIG. 13 is similar to the system of FIG. 10A in that the system of FIG. 13 includes a heat sink (1002), an integrated circuit (1010) installed on a PCB (1014), and TIM (1008) applied to the integrated circuit (1010). The integrated circuit (1010) includes a plurality of TIM detection points (1006), with each TIM detection point (1006) including a TIM detection device (1004) activated upon contact with TIM (1008) and providing a TIM detection signal (1016) to a TIM detection module (1012) upon activation for determination of the sufficiency of the TIM (1008) between the heat sink and the integrated circuit.

The system of FIG. 13 differs from the system of FIG. 10A, however, in that in the system of FIG. 13, each TIM detection device (1004) includes a mechanical switch (1202). The mechanical switch is closed prior to contact with the TIM (108). In the example of FIG. 13, the mechanical switch (602) is coupled to ground voltage when closed. The TIM detection device is activated by physically opening, by the TIM (1008), the mechanical switch.

Figure 14:
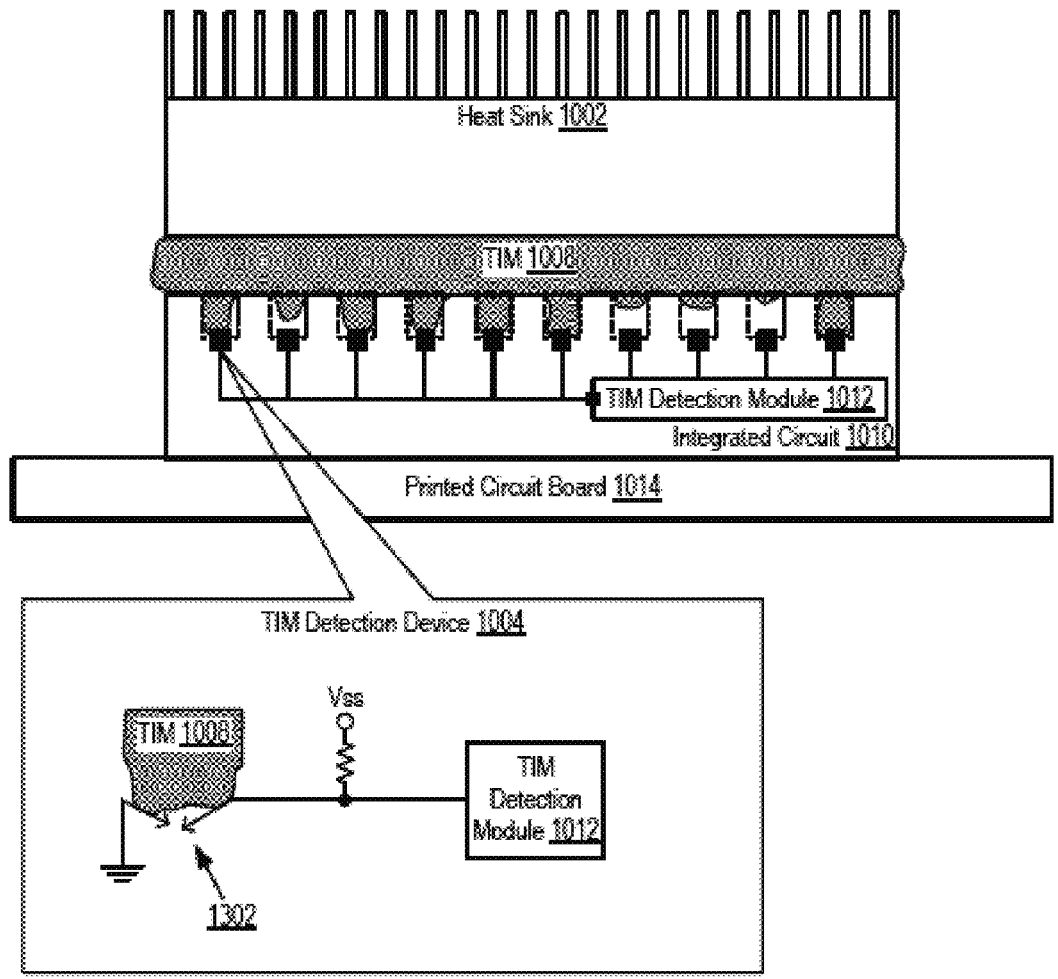
FIG. 14 sets forth a perspective view of the example system of FIG. 13, after installation of the heat sink.

For further explanation, FIG. 14 sets forth a perspective view of the example system of FIG. 13, after installation of the heat sink. In the example of FIG. 14, upon installation of the heat sink (1002) on the integrated circuit (1010) and the TIM (1008), TIM (1008) is received in one or more of the TIM detection points (1006) and the TIM (1008) activates a TIM detection device (1004) in each of the TIM detection points receiving the TIM (1008). In the example of FIG. 14, activating a TIM detection device (1004) includes physically opening the mechanical switch (1302) by the TIM (1008). As mentioned above, the mechanical switch (1302) is coupled to ground voltage when closed. The voltage experienced by the TIM detection module (1012) from the TIM detection device (1004), therefore, prior to contact between the TIM and the mechanical switch, is a ground voltage. After the TIM physically opens the mechanical switch (1302), the voltage experienced on the signal line (1016) by the TIM detection module (1012) is a source voltage (Vss). The alternation between a ground voltage and the source voltage indicates to the TIM detection module (1012) that TIM is present in the TIM detection point that includes the opened mechanical switch.

Figure 15:
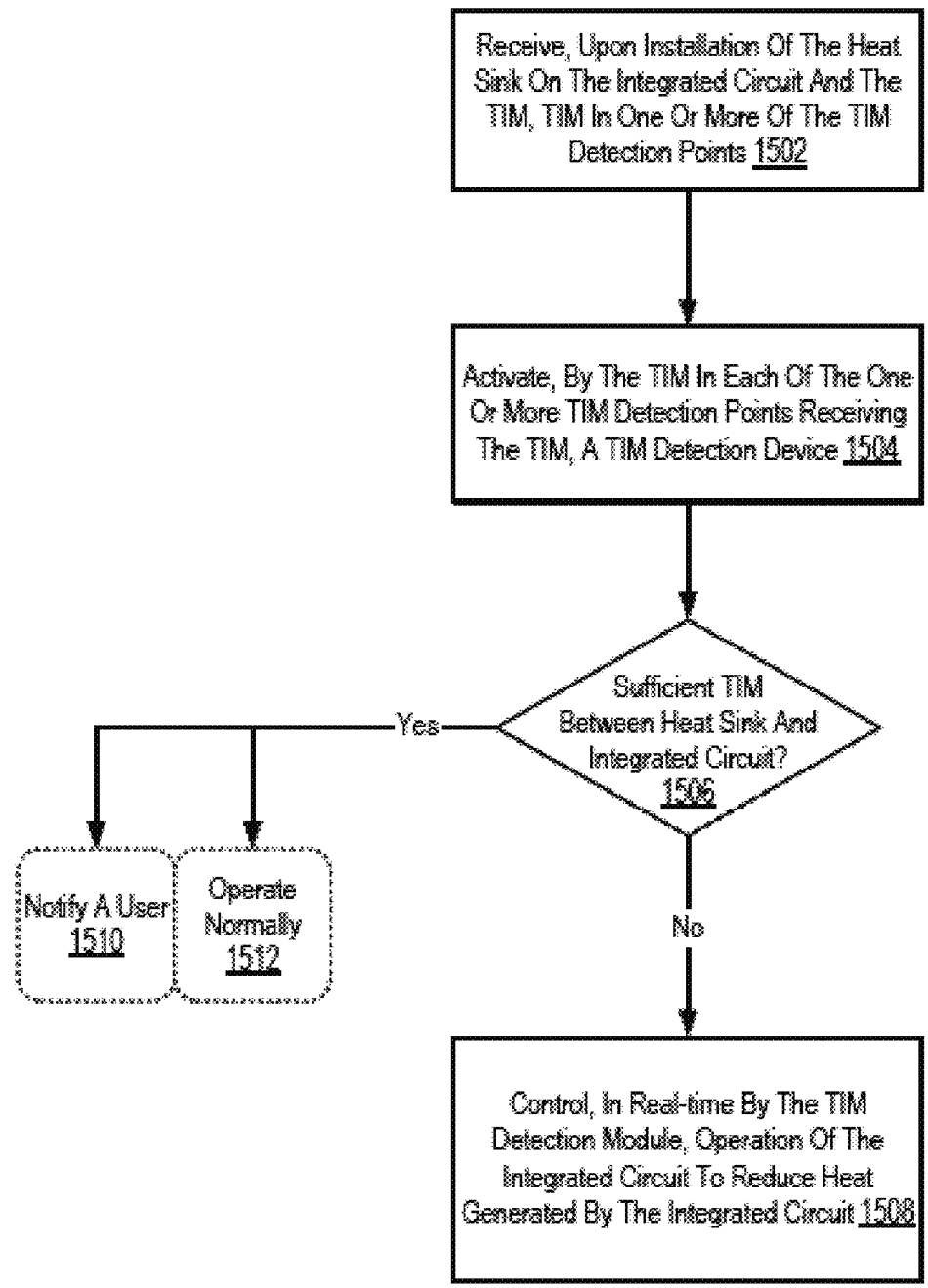
FIG. 15 sets forth a flow chart illustrating an exemplary method for detecting TIM between a heat sink and an integrated circuit according to embodiments of the present invention in which TIM detection points and TIM detection devices are implemented in an integrated circuit.

For further explanation, FIG. 15 sets forth a flow chart illustrating an exemplary method for detecting TIM between a heat sink and an integrated circuit according to embodiments of the present invention in which TIM detection points and TIM detection devices are implemented in an integrated circuit. The example method of FIG. 15 is carried out in a system similar to that depicted in the examples of FIGS. 10A and 10B which includes a heat sink and an integrated circuit, where the integrated circuit includes a plurality of TIM detection points, each TIM detection point is adapted to receive TIM upon installation of the heat sink, and each TIM detection point includes a TIM detection device configured to be activated upon contact with TIM.

The method of FIG. 9 includes receiving (1502), upon installation of the heat sink on the integrated circuit and the TIM, TIM in one or more of the TIM detection points; activating (1504), by the TIM in each of the one or more TIM detection points receiving the TIM, a TIM detection device; and determining (1506), by a TIM detection module of the integrated circuit in dependence upon the activations of the TIM detection devices, sufficiency of the TIM between the heat sink and the integrated circuit.

If the TIM detection module determines that the TIM is sufficient, the method of FIG. 15 continues by either notifying (1510) a user of the sufficiency of the TIM or operating (1512) the integrated circuit normally. Responsive to determining insufficiency of the TIM, by contrast, the method of FIG. 15 continues by controlling (1508), in real-time by the TIM detection module, operation of the integrated circuit to reduce heat generated by the integrated circuit.

In some embodiments, the integrated circuit may be implemented as a computer processor. In such embodiments, controlling (1508) operation of the integrated circuit in real-time to reduce heat generated by the integrated circuit may be carried out by throttling the computer processor.

In some embodiments, the integrated circuit is implemented as a computer processor, the computer processor including a number of functional units, a number of cache memory devices, and a number of registers. In such an embodiment controlling (1508) operation of the integrated circuit in real-time to reduce heat generated by the integrated circuit may be carried out by dispatching instructions among functional units, utilizing cache memory devices, and utilizing registers so as to avoid components of the computer processor having physical locations with insufficient TIM.

In some embodiments, the integrated circuit is implemented as a multi-core computer processor. In such an embodiment, controlling (1508) operation of the integrated circuit in real-time to reduce heat generated by the integrated circuit may be carried out by distributing execution of computer program instructions among the cores of the computer processor so as to avoid cores having a physical location with insufficient TIM.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A method of detecting thermal interface material (TIM) between a heat sink and an integrated circuit that comprises a plurality of TIM detection points, the method comprising:
   receiving, upon installation of the heat sink on the integrated circuit and the TIM in one or more of the TIM detection points, wherein each of the one or more TIM detection points includes a TIM detection device;
   activating, in each of the one or more TIM detection points receiving the TIM, a TIM detection device;
   determining, in dependence upon the activations of the TIM detection devices, sufficiency of the TIM between the heat sink and the integrated circuit; and
   responsive to determining that the TIM between the heat sink and the integrated circuit is insufficient, controlling, in real-time, operation of the integrated circuit to reduce heat generated by the integrated circuit.

2. The method of claim 1 wherein determining sufficiency of the TIM between the heat sink and the integrated circuit further comprises determining whether the number of activated TIM detection devices exceeds a predetermined threshold.

3. The method of claim 1 wherein determining sufficiency of the TIM between the heat sink and the integrated circuit further comprises determining whether the positions of the activated TIM detection devices indicate a sufficient coverage area of the TIM.

4. The method of claim 1 wherein the integrated circuit further comprises a computer processor, the computer processor including a number of functional units, a number of cache memory devices, a number of registers, and controlling operation of the integrated circuit in real-time to reduce heat generated by the integrated circuit further comprises dispatching instructions among functional units, utilizing cache memory devices, and utilizing registers so as to avoid components of the computer processor having physical locations with insufficient TIM.

5. The method of claim 1 wherein the integrated circuit further comprises a multi-core computer processor and controlling operation of the integrated circuit in real-time to reduce heat generated by the integrated circuit further comprises distributing execution of computer program instructions among the cores of the computer processor so as to avoid cores having a physical location with insufficient TIM.

6. The method of claim 1 wherein the integrated circuit further comprises a computer processor and controlling operation of the integrated circuit in real-time to reduce heat generated by the integrated circuit further comprises throttling the computer processor.

7. The method of claim 1 wherein:
   a casing of the integrated circuit is electrically coupled to a ground voltage;
   the TIM is electrically conductive and is electrically coupled to the integrated circuit casing;
   each TIM detection device comprises an electrical probe, the electrical probe having a source voltage prior to electrically coupling to the TIM; and
   activating the TIM detection device further comprises electrically coupling the electrical probe to the integrated circuit casing and the ground voltage, altering the voltage level at the electrical probe from the source voltage to the ground voltage; and
   determining sufficiency of the TIM between the heat sink and the integrated circuit further comprises detecting, for each TIM detection point receiving the TIM, the alteration of the voltage level of each electrical probe.

8. The method of claim 1 wherein:
   each TIM detection device comprises a mechanical switch, the mechanical switch closed prior to receiving TIM; and
   activating the TIM detection device further comprises physically opening the mechanical switch; and
   determining sufficiency of the TIM between the heat sink and the integrated circuit further comprises detecting the opening of each mechanical switch activated upon receiving the TIM in the TIM detection point.

9. An apparatus for detecting thermal interface material (TIM) between a heat sink and an integrated circuit that comprises plurality of TIM detection points, the apparatus comprising a computer processor, a computer memory operatively coupled to the computer processor, the computer memory having disposed within it computer program instructions that, when executed by the computer processor, cause the apparatus to carry out the steps of:
   receiving, upon installation of the heat sink on the integrated circuit and the TIM in one or more of the TIM detection points, wherein each of the one or more TIM detection points includes a TIM detection device;
   activating, in each of the one or more TIM detection points receiving the TIM, a TIM detection device; and
   determining, in dependence upon the activations of the TIM detection devices, sufficiency of the TIM between the heat sink and the integrated circuit; and
   responsive to determining that the TIM between the heat sink and the integrated circuit is insufficient, controlling, in real-time, operation of the integrated circuit to reduce heat generated by the integrated circuit.

10. The apparatus of claim 9 wherein determining sufficiency of the TIM between the heat sink and the integrated circuit further comprises determining whether the number of activated TIM detection devices exceeds a predetermined threshold.

11. The apparatus of claim 9 wherein determining sufficiency of the TIM between the heat sink and the integrated circuit further comprises determining whether the positions of the activated TIM detection devices indicate a sufficient coverage area of the TIM.

12. The apparatus of claim 9 wherein the integrated circuit further comprises a computer processor, the computer processor including a number of functional units, a number of cache memory devices, a number of registers, and controlling operation of the integrated circuit in real-time to reduce heat generated by the integrated circuit further comprises dispatching instructions among functional units, utilizing cache memory devices, and utilizing registers so as to avoid components of the computer processor having physical locations with insufficient TIM.

13. The apparatus of claim 9 wherein the integrated circuit further comprises a multi-core computer processor and controlling operation of the integrated circuit in real-time to reduce heat generated by the integrated circuit further comprises distributing execution of computer program instructions among the cores of the computer processor so as to avoid cores having a physical location with insufficient TIM.

14. The apparatus of claim 9 wherein the integrated circuit further comprises a computer processor and controlling operation of the integrated circuit in real-time to reduce heat generated by the integrated circuit further comprises throttling the computer processor.

15. The apparatus of claim 9 wherein:
a casing of the integrated circuit is electrically coupled to a ground voltage;
the TIM is electrically conductive and is electrically coupled to the integrated circuit casing;
each TIM detection device comprises an electrical probe, the electrical probe having a source voltage prior to electrically coupling to the TIM; and
activating the TIM detection device further comprises electrically coupling the electrical probe to the integrated circuit casing and the ground voltage, altering the voltage level at the electrical probe from the source voltage to the ground voltage; and
determining sufficiency of the TIM between the heat sink and the integrated circuit further comprises detecting, for each TIM detection point receiving the TIM, the alteration of the voltage level of each electrical probe.

16. The apparatus of claim 9 wherein:
each TIM detection device comprises a mechanical switch, the mechanical switch closed prior to receiving TIM; and
activating the TIM detection device further comprises physically opening the mechanical switch; and
determining sufficiency of the TIM between the heat sink and the integrated circuit further comprises detecting the opening of each mechanical switch activated upon receiving the TIM in the TIM detection point.

17. A computer program product disposed upon a computer readable medium, the computer program product comprising computer program instructions that, when executed, cause a computer to carry out the steps of:
receiving, upon installation of a heat sink on an integrated circuit and the thermal interface material ('TIM'), TIM in one or more of the TIM detection points, wherein each of the one or more TIM detection points includes a TIM detection device;
activating, in each of the one or more TIM detection points receiving the TIM, a TIM detection device; and
determining, in dependence upon the activations of the TIM detection devices, sufficiency of the TIM between the heat sink and the integrated circuit; and
responsive to determining that the TIM between the heat sink and the integrated circuit is insufficient, controlling, in real-time, operation of the integrated circuit to reduce heat generated by the integrated circuit.

18. The computer program product of claim 17 wherein determining sufficiency of the TIM between the heat sink and the integrated circuit further comprises determining whether the number of activated TIM detection devices exceeds a predetermined threshold.

19. The computer program product of claim 17 wherein determining sufficiency of the TIM between the heat sink and the integrated circuit further comprises determining whether the positions of the activated TIM detection devices indicate a sufficient coverage area of the TIM.

20. The computer program product of claim 17 wherein the integrated circuit further comprises a computer processor, the computer processor including a number of functional units, a number of cache memory devices, a number of registers, and controlling operation of the integrated circuit in real-time to reduce heat generated by the integrated circuit further comprises dispatching instructions among functional units, utilizing cache memory devices, and utilizing registers so as to avoid components of the computer processor having physical locations with insufficient TIM.

21. The computer program product of claim 17 wherein the integrated circuit further comprises a multi-core computer processor and controlling operation of the integrated circuit in real-time to reduce heat generated by the integrated circuit further comprises distributing execution of computer program instructions among the cores of the computer processor so as to avoid cores having a physical location with insufficient TIM.

22. The computer program product of claim 17 wherein the integrated circuit further comprises a computer processor and controlling operation of the integrated circuit in real-time to reduce heat generated by the integrated circuit further comprises throttling the computer processor.

23. The computer program product of claim 17 wherein:
a casing of the integrated circuit is electrically coupled to a ground voltage;
the TIM is electrically conductive and is electrically coupled to the integrated circuit casing;
each TIM detection device comprises an electrical probe, the electrical probe having a source voltage prior to electrically coupling to the TIM; and
activating the TIM detection device further comprises electrically coupling the electrical probe to the integrated circuit casing and the ground voltage, altering the voltage level at the electrical probe from the source voltage to the ground voltage; and
determining sufficiency of the TIM between the heat sink and the integrated circuit further comprises detecting, for each TIM detection point receiving the TIM, the alteration of the voltage level of each electrical probe.

24. The computer program product of claim 17 wherein:
each TIM detection device comprises a mechanical switch, the mechanical switch closed prior to receiving TIM; and activating the TIM detection device further comprises physically opening the mechanical switch; and determining sufficiency of the TIM between the heat sink and the integrated circuit further comprises detecting the opening of each mechanical switch activated upon receiving the TIM in the TIM detection point.

25. An integrated circuit comprising:

a plurality of thermal interface material ('TIM') detection points, each TIM detection point adapted to receive TIM upon installation of a heat sink on the integrated circuit and the TIM, each TIM detection point comprises a TIM detection device activated upon contact with TIM; and a TIM detection module configured to:
receive a TIM detection signal from each TIM detection device upon contact between TIM and the TIM detection device and to determine, in dependence upon the received TIM detection signals, the sufficiency of the TIM between the heat sink and the integrated circuit;

responsive to determining that the TIM between the heat sink and the integrated circuit is insufficient, controlling operation of the integrated circuit to reduce heat generated by the integrated circuit.

26. The integrated circuit of claim 25 wherein:

a casing of the integrated circuit is electrically coupled to a ground voltage;

the TIM is electrically conductive and is electrically coupled to the integrated circuit casing;

each TIM detection device comprises an electrical probe, the electrical probe having a source voltage prior to electrically coupling to the TIM; and the TIM detection device is activated upon contact with the TIM by electrically coupling the electrical probe to the TIM, integrated circuit casing, and the ground voltage, altering the voltage level at the electrical probe from the source voltage to the ground voltage.

27. The integrated circuit of claim 25 wherein:

each TIM detection device comprises a mechanical switch, the mechanical switch closed prior to receiving TIM; and the TIM detection device is activated by physically opening the mechanical switch.

* * * * *